US008303807B2

(12) United States Patent
Zhang

(10) Patent No.: US 8,303,807 B2
(45) Date of Patent: Nov. 6, 2012

(54) DIALYSER WITH MEASURING DEVICES FOR MONITORING THE BLOOD PRESSURE, METHOD OF DETERMINING THE BLOOD PRESSURE AND A STORAGE MEDIUM FOR USE IN A DIALYSER

(75) Inventor: Wei Zhang, Niederwerrn (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 805 days.

(21) Appl. No.: 12/224,864

(22) PCT Filed: Mar. 5, 2007

(86) PCT No.: PCT/DE2007/000406
§ 371 (c)(1),
(2), (4) Date: Sep. 17, 2008

(87) PCT Pub. No.: WO2007/101431
PCT Pub. Date: Sep. 13, 2007

(65) Prior Publication Data
US 2009/0050544 A1   Feb. 26, 2009

(30) Foreign Application Priority Data
Mar. 7, 2006   (DE) .......................... 10 2006 010 813

(51) Int. Cl.
*B01D 61/12* (2006.01)
(52) U.S. Cl. .... 210/90; 210/96.2; 210/143; 210/321.65; 210/646; 600/485; 600/500; 600/501
(58) Field of Classification Search .................... 210/85, 210/87, 90, 143, 321.65, 646, 96.2; 600/483, 600/485–488, 490, 500–503
See application file for complete search history.

(56) References Cited

U.S. PATENT DOCUMENTS
5,293,874 A * 3/1994 Takahashi et al. ............ 600/500
(Continued)

FOREIGN PATENT DOCUMENTS
DE   44 27 991   2/1996
(Continued)

OTHER PUBLICATIONS
International Search Report.

*Primary Examiner* — Joseph Drodge
(74) *Attorney, Agent, or Firm* — Collard & Roe, P.C.

(57) ABSTRACT

The invention relates to a dialyser having a blood-pressure measuring unit assigned to the dialyser, a pulse-wave-transit-time measuring system assigned to the dialyser and an evaluation unit, the evaluation unit being configured such that a signal representing the blood pressure can be derived from this pulse wave transit time; the parameters describing the relationship between the pulse wave transit time and the blood pressure can be determined from a plurality of measurements made by the blood-pressure measuring unit and simultaneous measurements made by the pulse-wave-transit-time measuring system, it being possible to determine at least two of these pairs of measured values at times when the absolute and/or the relative pulse-wave-transit-time deviation is above a threshold value. The invention relates further to a method of determining the parameters describing the relationship between a pulse-wave-transit-time signal and a blood-pressure-measurement signal, a signal representing the blood pressure subsequently being derived from the pulse wave transit time; the parameters describing the relationship between the pulse wave transit time and the blood pressure are determined from blood-pressure-measurement-signal values and simultaneous pulse-wave-transit-time values, at least two of these pairs of measured values being obtained at points in time when the absolute and/or the relative deviation of the pulse wave transit time and/or of the blood pressure is above a threshold value.

10 Claims, 3 Drawing Sheets

U.S. PATENT DOCUMENTS

| | | | |
|---|---|---|---|
| 5,603,329 A * | 2/1997 | Hosaka et al. | 600/493 |
| 5,830,131 A | 11/1998 | Caro et al. | |
| 5,876,348 A * | 3/1999 | Sugo et al. | 600/490 |
| 5,921,936 A * | 7/1999 | Inukai et al. | 600/490 |
| 6,527,728 B2 | 3/2003 | Zhang | |
| 6,736,789 B1 * | 5/2004 | Spickermann | 604/5.01 |
| 6,852,083 B2 * | 2/2005 | Caro et al. | 600/485 |
| 6,878,272 B2 * | 4/2005 | Kawaguchi | 210/321.65 |
| 6,878,273 B2 * | 4/2005 | Kawaguchi | 210/321.65 |
| 7,594,893 B2 * | 9/2009 | Tao et al. | 600/500 |
| 2002/0193691 A1 | 12/2002 | Sato | |
| 2004/0111294 A1 * | 6/2004 | McNally et al. | 705/2 |
| 2004/0249292 A1 * | 12/2004 | Davis et al. | 600/481 |
| 2006/0047193 A1 * | 3/2006 | Zhang | 600/368 |
| 2007/0167852 A1 * | 7/2007 | Sugo et al. | 600/513 |

FOREIGN PATENT DOCUMENTS

| | | |
|---|---|---|
| DE | 198 29 544 | 1/2000 |
| DE | 101 14 383 | 10/2002 |
| EP | 0 875 200 | 11/1998 |
| EP | 0 911 044 | 4/1999 |
| EP | 1 199 029 | 4/2002 |

* cited by examiner

DIALYSER WITH MEASURING DEVICES FOR MONITORING THE BLOOD PRESSURE, METHOD OF DETERMINING THE BLOOD PRESSURE AND A STORAGE MEDIUM FOR USE IN A DIALYSER

CROSS REFERENCE TO RELATED APPLICATIONS

This application is the National Stage of PCT/DE2007/000406 filed on Mar. 5, 2007, which claims priority under 35 U.S.C. §119 of German Application No. 10 2006 010 813.2 filed on Mar. 7, 2006. The international application under PCT article 21(2) was not published in English.

The invention relates to a dialyser, a method of determining the blood pressure, and a storage medium for use in a dialyser.

Dialysers of this kind, in which the blood pressure is measured automatically by the dialyser during the dialysis therapy, are known. The term dialyser as used here includes all for renal-replacement-therapy machines that intervene in a patient's fluid balance, irrespective of whether the machine is a haemodialysis, haemofiltration, haemodiafiltration or other such machine.

Drops in blood pressure during dialysis therapy are among the most frequent complications. They occur during some 20-30% of therapy sessions. A hypotonic episode of this kind often develops suddenly and may result, firstly, in the patient's losing consciousness and, secondly, in the necessity of discontinuing the therapy session and even of expensive and complicated intervention. In consequence, the patient's morbidity and mortality are very negatively influenced.

A number of regulatory mechanisms are needed to maintain a constant blood pressure. These may be impaired both by haemodialysis therapy and by the various earlier and concomitant diseases suffered by the patient.

Ultrafiltration causes a decrease in the plasma volume. If the subject does not manage to restore the plasma volume from the interstitial space, the heart's filling pressure and the blood pressure sink. This will happen all the more quickly if high ultrafiltration rates are required. Drops in blood pressure are most frequently encountered in patients with cardiovascular limitations, as in elderly people, patients with myocardial insufficiency or diabetic nephropathy and patients taking circulatory medication.

There are various known ways of configuring dialysers so that a drop in blood pressure can be recognized early on and/or prevented. For one, there are monitoring devices that measure the relative blood volume during the dialysis therapy and, if necessary, regulate the ultrafiltration. For another, there are monitoring devices that continuously monitor changes in a patient's blood pressure by determining the pulse wave transit time (PTT) and, if necessary, regulate the ultrafiltration. The time that a pressure pulse takes to travel along a patient's vessel from one point to another is a function of the blood pressure. This time can be determined with comparative ease. As start signal, an ECG signal may be used, while as stop signal, use may be made of an optical pulsometer located at a peripheral point away from the heart. This procedure has already been described in the U.S. Pat. No. 6,736,789, to the disclosed subject matter of which reference is made explicitly.

A method for repeatedly calibrating parameters is known from the U.S. Pat. No. 6,852,083. According to this method, a trigger signal is determined from the derived signal (for example, blood pressure derived from the pulse wave transit time). If this trigger signal exceeds a given threshold value, a renewed calibration is performed. The U.S. Pat. No. 6,852,083 does not explain how this trigger-signal criterion is fulfilled.

The U.S. Pat. No. 5,603,329 describes how to determine the parameters of a linear equation from blood pressure measurements obtained at defined times and from the pulse wave transit time. To this end, a point in time on a systolic pulse wave is identified and the corresponding blood pressure measured. In addition, the point in time on the diastolic pulse wave corresponding to the systolic pulse wave is identified, and again, the corresponding blood pressure measured. These two pairs of measured values are then used to determine the parameters of the linear equation that describes the relationship between the pulse wave transit time and the blood pressure. Once these parameters have been defined, they can be used to determine the blood pressure from the measured pulse wave transit time. The gradient of the straight lines may also be used as an indication of the patient's degree of arteriosclerosis.

Equation (1) is an example of a linear description of the relationship between the BP and the PTT, $$BP(t) = m - n \cdot PTT(t) \quad (1)$$

where m and n are patient-dependent constants that may change in the long term. It follows from Equation (1) that $$\frac{BP(0) - BP(i)}{BP(0)} = K \cdot \frac{PTT(i) - PTT(0)}{PTT(0)} \quad (2)$$

$$K = \frac{n \cdot PTT(0)}{m - n \cdot PTT(0)} \quad (3)$$

where
  BP(0) is the blood pressure (mmHg) measured at dialysis time $t_0$
  PIT(0) is the pulse wave transit time (ms) measured at dialysis time $t_0$
  BP(i) is the blood pressure (mmHg) measured at dialysis time $t_i$
  PIT(i) is the pulse wave transit time (ms) measured at dialysis time $t_i$ Equation (2) means that the relative PTT change and the relative BP change are related via the parameter K. K is a function of m and n. The constants m and n have to be determined in two calibration measurements in order that the relative PTT change can be converted precisely to BP change.

The method of monitoring blood pressure by means of a conventional cuff measurement is also known. The patient may find it unpleasant that the cuff has to be "pumped up" at regular intervals (e.g. every 30 minutes) in order to perform the measurement. Another, more important, disadvantage of cuff measurements is that a radical drop in blood pressure is difficult to detect due to the measurements being discontinuous.

The object of this invention is to propose a procedure for easy (and for the patient, comfortable) measurement of the absolute blood pressure and/or the change in blood pressure.

The problem is solved according to the invention by a dialyser according to which a blood-pressure measuring unit, a pulse-wave-transit-time measuring system and an evaluation unit are assigned to said dialyser. According to this invention, the evaluation unit is configured such that the parameters describing the relationship between the pulse wave transit time and the blood pressure can be determined from measurements made by the blood-pressure measuring unit and simultaneous measurements made by the pulse-wave-transit-time measuring system, it being possible to determine at least two of these pairs of measured values at times when the absolute and/or the relative pulse-wave-transit-time deviation is above a threshold value.

In a preferred embodiment of the invention the absolute and/or relative deviation is understood as to be the always positive value of the amount of the deviation. Without evaluation of the always positive value of the amount of the deviation but with evaluation of the deviation itself additional effort has to be done to take into account the strong fall off of the measurement values under a lower threshold value. Evaluation of the always positive value of the amount of the deviation means that a strong fall off of the measurement values can easily be taken into account.

It has been found advantageous if, for determination of the parameters describing the relationship between at least two pairs of measured values, the blood pressure values differ by a sufficiently large amount, so that it may be assumed that the parameters, in particular, can be determined with sufficient accuracy.

The relationship between the pulse wave transit time and the blood pressure may be parametrized, for example as a linear dependence in the form of a straight line.

If parameters have already been determined on the basis of earlier therapy sessions, these parameters may be used to obtain a blood pressure value from the measured pulse wave transit times. In this case, the criterion for the determination of further pairs of measured values can, with respect to the threshold, be related to the blood pressure itself, this being a value derived from the measured pulse wave transit time.

If no parameters have as yet been determined, a threshold value determined from the pulse wave transit time may be used. This may be an absolute difference in the pulse wave transit times, or also a relative deviation of the pulse wave transit times.

According to another embodiment of the proposed solution, the pulse wave transit time is measured and monitored in relation to the threshold value. Once the threshold criterion applies, a blood-pressure measurement by the measuring unit can be initiated. This more detailed configuration has the advantage that it is unnecessary to measure the blood pressure at regular intervals in order to be able to determine the parameters, for example on completion of a measuring phase. If the threshold criterion for the pulse wave transit time is fulfilled in the proposed more detailed embodiment, the appropriate blood-pressure measurement can be initiated.

Apart from the pairs of measured values derived in this way, other pairs of measured values may also be recorded during a dialysis therapy session. In this case, the parameters for describing the relationship may be determined from an overdetermined equation system by means of statistical methods, for instance the smallest-error-squares method.

In the case of a dialyser, it makes sense to perform an initial measurement at the start of the therapy session. At this point in time, the patient's blood pressure is high because the blood has not yet been withdrawn for treatment. The threshold values for the pulse wave transit time and the blood pressure are reached automatically during the dialysis session, as would be expected when blood is removed and the blood pressure drops as a result. It proves especially beneficial here if parameter determination is made dependent on the threshold values. It has been found that these criteria defined by the threshold values are fulfilled by an initial measurement performed prior to blood removal and at least one additional measurement performed after the extracorporeal circuit has filled with blood withdrawn from the patient.

Since a dialyser also has means for withdrawing fluid from the patient's extracorporeal blood circuit, the criteria defined by the threshold values are also fulfilled during dialysis. The same applies after the extracorporeal blood is returned on completion of the dialysis session. There is accordingly no need for any additional measures whatsoever.

The evaluation unit may be configured such as to allow pulse-wave-transit-time and blood pressure measurements to be recorded specifically at the following times: before the patient is connected up to the extracorporeal circuit, after the patient has been connected up and the extracorporeal circuit has filled with blood but before dialysis has begun, on completion of dialysis and/or following the return of the blood to the patient when dialysis has been completed. Dialysis-inherent blood-pressure changes occur at all of these times, making these times particularly suitable for fulfilling the threshold criterion. The evaluation unit is expediently connected up to a correspondingly configured dialyser control unit, which is also connected to the fluid-withdrawing means. Provision may also be made for the fluid-withdrawing means to withdraw fluid specifically to effect a requested blood-pressure change, as well as to withdraw fluid for normal therapeutic purposes.

An instruction to the effect that the patient's position should be altered (from supine to lateral position or vice versa) so as to effect a blood-pressure change may be issued additionally via an output unit, for instance on a screen or via a voice system. This measure may be provided as an additional aid, although it has been found that the dialysis therapy itself will cause the threshold values to be exceeded.

For parameter determination in the embodiment described in the invention, the pairs of measured values can be weighted according to the times the values were recorded, the weighting being weaker for pairs of measured values recorded further back in time.

As the parameters can change with time, the procedure according to the invention ensures that the most recent measured values are weighted more strongly during parameter determination. The parameters are thus sufficiently recent.

In the embodiment according to the invention, the maximum and minimum blood pressures measured, together with the corresponding pulse wave transit times, can be used to determine the parameters describing the relationship between the pulse wave transit time and the blood pressure.

This procedure makes for relatively easy determination of the parameters from the minimum and maximum values.

In the embodiment according to the invention, only such pairs of measured values as are obtained within a given time window can be used to determine the parameters describing the relationship.

This is a special variant of weighting the pairs of measured values as a function of the times at which the pairs of measured values were obtained. The "weighting" of values obtained before a given time window is set to zero, so that these pairs of measured values no longer count.

There is also an embodiment in which a data input unit is assigned or assignable to the dialyser, said input unit serving to supply pairs of values obtained by the measuring unit and the measuring system during earlier therapy sessions with the same patient to the evaluation unit from a storage medium.

The data input unit may be physically connected to the dialyser. It is also possible to provide a port for connection to a portable data input unit that can then be used successively for a plurality of dialysers.

This solution offers the advantage that the data need not be stored in a computer at the dialysis centre. Instead, they can be stored on a storage medium and kept in the patient's file. At the next treatment session, the required data can simply be made available again.

In the embodiment according to the invention, the data input unit is simultaneously a data output unit with which the pairs of measured values from the current therapy session can be written onto the storage medium.

These data, too, are then advantageously available again for future therapy sessions.

In the embodiment of a method for determining the parameters describing the relationship between a pulse-wave-transit-time signal and a blood-pressure-measurement signal, the parameters describing the relationship between the pulse wave transit time and the blood pressure are determined according to this invention from blood-pressure-measurement-signal values and simultaneous pulse-wave-transit-time values, at least two of these pairs of measured values being obtained at points in time when the absolute and/or the relative pulse-wave-transit-time deviation is above a threshold value.

It has been found advantageous if, for determination of the parameters describing the relationship between at least two pairs of measured values, the blood-pressure values differ by a sufficiently large amount. Provided the parameters define a straight line, it may be assumed that also, and in particular, the gradient of the straight line can be determined with a sufficient degree of accuracy.

If parameters have already been determined on the basis of earlier therapy sessions, these parameters may be used to obtain a blood pressure value from the measured pulse wave transit times. In this case, the criterion for the determination of further pairs of measured values can, with respect to the threshold, be related to the blood pressure itself, this being a value derived from the measured pulse wave transit time.

If no parameters have as yet been determined, a threshold value determined from the pulse wave transit time may be used. This may be an absolute difference in the pulse wave transit times, or also a relative deviation of the pulse wave transit times.

According to another embodiment of the proposed solution, the pulse wave transit time is measured and monitored in relation to the threshold value. Once the threshold criterion applies, a blood-pressure measurement by the measuring unit can be initiated. This more detailed configuration has the advantage that it is unnecessary to measure the blood pressure at regular intervals in order to be able to determine the parameters, for example on completion of a measuring phase. If the threshold criterion for the pulse wave transit time is fulfilled in the proposed more detailed embodiment, the appropriate blood-pressure measurement can be initiated.

Apart from the pairs of measured values derived in this way, other pairs of measured values may also be recorded during a dialysis therapy session. In this case, the parameters for describing the relationship may be determined from an overdetermined equation system by means of statistical methods, for instance the smallest-error-squares method.

In the case of a dialyser, it makes sense to perform an initial measurement at the start of the therapy session. At this point in time, the patient's blood pressure is high because the blood has not yet been withdrawn for treatment. The threshold values for the pulse wave transit time and the blood pressure are reached automatically during the dialysis session, as would be expected when blood is removed and the blood pressure drops as a result. It proves especially beneficial here if parameter determination is made dependent on the threshold values. It has been found that these criteria defined by the threshold values are fulfilled by an initial measurement performed prior to blood withdrawal and at least one additional measurement performed after the extracorporeal circuit has filled with blood withdrawn from the patient.

Since a dialyser also has means for withdrawing fluid from the patient's extracorporeal blood circuit, the criteria defined by the threshold values are also fulfilled during dialysis. The same applies after the extracorporeal blood is returned on completion of the dialysis session. There is accordingly no need for any additional measures whatsoever.

An instruction to the effect that the patient's position should be altered (from supine to lateral position or vice versa) so as to effect a blood-pressure change may be issued additionally via an output unit, for instance on a screen or via a voice system. This measure may be provided as an additional aid, although it has been found that the dialysis therapy itself will cause the threshold values to be exceeded.

For parameter determination in the embodiment described in the invention, the pairs of measured values are weighted according to the times the values were recorded, the weighting being weaker for pairs of measured values recorded further back in time.

As the parameters can change with time, the procedure according to the invention ensures that the most recent measured values are weighted more strongly during parameter determination. The parameters are thus sufficiently recent.

In the embodiment according to the invention, the maximum and minimum blood pressures measured, together with the corresponding pulse wave transit times, are used to determine the parameters describing the relationship between the pulse wave transit time and the blood pressure.

This procedure makes for relatively easy determination of the parameters from the minimum and maximum values.

In the embodiment according to the invention, only such pairs of measured values as are obtained within a given time window are used to determine the parameters describing the relationship.

This is a special variant of weighting the pairs of measured values as a function of the times at which the pairs of measured values were obtained. The "weighting" of values obtained before a given time window is set to zero, so that these pairs of measured values no longer count.

Also the invention relates to a storage medium for a dialyser.

The advantage of a storage medium of this kind is that the data pertaining to the individual measurements are available for subsequent therapy sessions.

According to the invention, the storage medium may be magnetic, optical or electrical. It has proved beneficial here to use standard technologies, so that these can be implemented immediately with the new application. The storage medium may, for instance, be a storage medium on which other medically relevant data, for example, data concerning other clinical pictures or to do with the organisation and financial settlement of medical treatment costs are stored.

An embodiment of the invention is explained in more detail below.

The parameters m and n in Equation (1) are patient and time-dependent and can be determined as follows by means of two calibration measurements:

$$BP_{max} = m - n \cdot PTT_{max} \quad (4)$$

$$BP_{min} = m - n \cdot PTT_{min} \quad (5)$$

where
$BP_{max}$ is the measured maximum blood pressure,
$PTT_{max}$-$BP_{max}$ is the corresponding measured PTT,
$BP_{min}$ is the measured minimum blood pressure, $PTT_{min}$–$BP_{min}$ is the corresponding measured PTT,
From Equations (4) and (5) we obtain $$n = \frac{BP_{max} - BP_{min}}{PTT_{min} - PTT_{max}} \quad (6)$$

$$m = \frac{BP_{max} \cdot PTT_{min} - BP_{min} \cdot PTT_{max}}{PTT_{min} - PTT_{max}} \quad (7)$$

Taking a wide range of applicability for Equation (1) into account, the criterion $$|BP(t_{k2}) - BP(t_{k1})| \geq TH_{Bp} \quad (8)$$

should be fulfilled for a calibration. In this context, $TH_{Bp}$ is a pre-defined threshold value for the blood-pressure difference, e.g. $TH_{BP}$=30 mmHg.

The relationship between the pulse wave transit time and the blood pressure is shown as a linear relationship, not in the sense of a concluding limitation but merely as a concrete embodiment.

The calibration data can be determined during the usual course of a haemodialysis session. A change in the patient's blood pressure may be generated here by appropriately changing the patient's position or by modifying the ultrafiltration rate. However, it is also possible to obtain a change in the patient's blood pressure during the normal course of the dialysis session.

For the continued explanation of the invention, it is assumed that
a) a conventional oscillometric blood pressure monitor with a cuff is integrated in the dialyser and that
b) a patient card is at hand for transferring data from therapy session to therapy session.

BRIEF DESCRIPTION OF THE DRAWINGS

The present invention will now be further explained by reference to the following detailed description of preferred embodiments of the invention when considered in conjunction with the accompanying drawings, in which:

FIG. 1 is a flow chart for the calibration of the parameters describing the relationship; in the embodiment described here, this relationship is linear.

After the start of dialysis, depicted as Step 101, the data are first read out from a patient card and stored in the dialyser (Step 102). The data include
 (Date$_0$, m$_0$, n$_0$)—constants in Equation (1) with date
 (Date$_{min0}$, BP$_{min0}$, PTT$_{min0}$)—previously registered minimum BP and corresponding PTT with date
 (Date$_{max0}$, BP$_{max0}$, PTT$_{max0}$)—previously registered maximum BP and corresponding PTT with date Following the start of dialysis, a case-by-case decision is made (Step 103) depending on whether the parameters m and n have already been determined during previous therapy sessions. If this is the case, the ongoing flowchart "B" is followed (Step 104), which is explained in FIG. 3. If the parameters m and n have not yet been determined, these will still have the value 0. In this case, the check performed in Step 103 will be followed by the flowchart "A" (Step 105), which is explained in FIG. 2.

Once the appropriate flowchart "A" or "B" has been worked through, a transfer of the parameters and of other data is effected (Step 106). These are:
 Date$_0$=Date, m$_0$=m, n$_0$=n
 Date$_{min\,0}$=Date$_{min}$, BP$_{min\,0}$=BP$_{min}$, PTT$_{min\,0}$=PTT$_{min}$
 Date$_{max\,0}$=D=Date$_{max}$, BP$_{max\,0}$=BP$_{max}$, PTT$_{max\,0}$=PTT$_{max}$
 where Date=Date$_{max}$ oder Date=Date$_{min}$, depending on which date is further back in time.

In Step 107, the calibration data and the values determined for the parameters m and n are stored as follows on the patient card:
 (Date$_0$, m$_0$, n$_0$)
 (Date$_{min\,0}$, BP$_{min\,0}$, PTT$_{min\,0}$)
 (Date$_{max\,0}$, BP$_{max\,0}$, PTT$_{max\,0}$).

Figure 1:
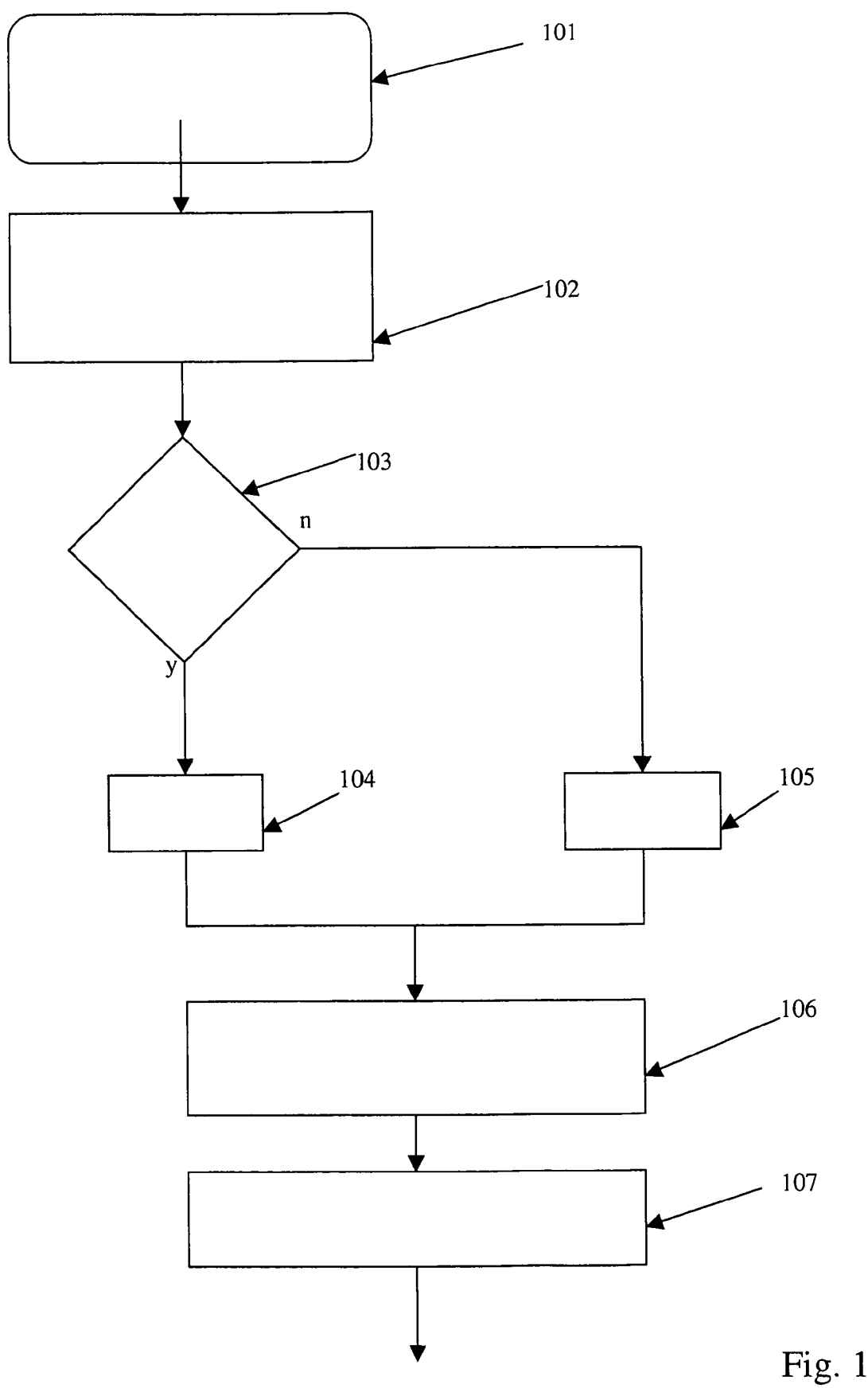
FIG. 1 is a flowchart for the calibration of the parameters describing the relationship.

The program flow shown in FIG. 1 ends at Step 108.

Figure 2:
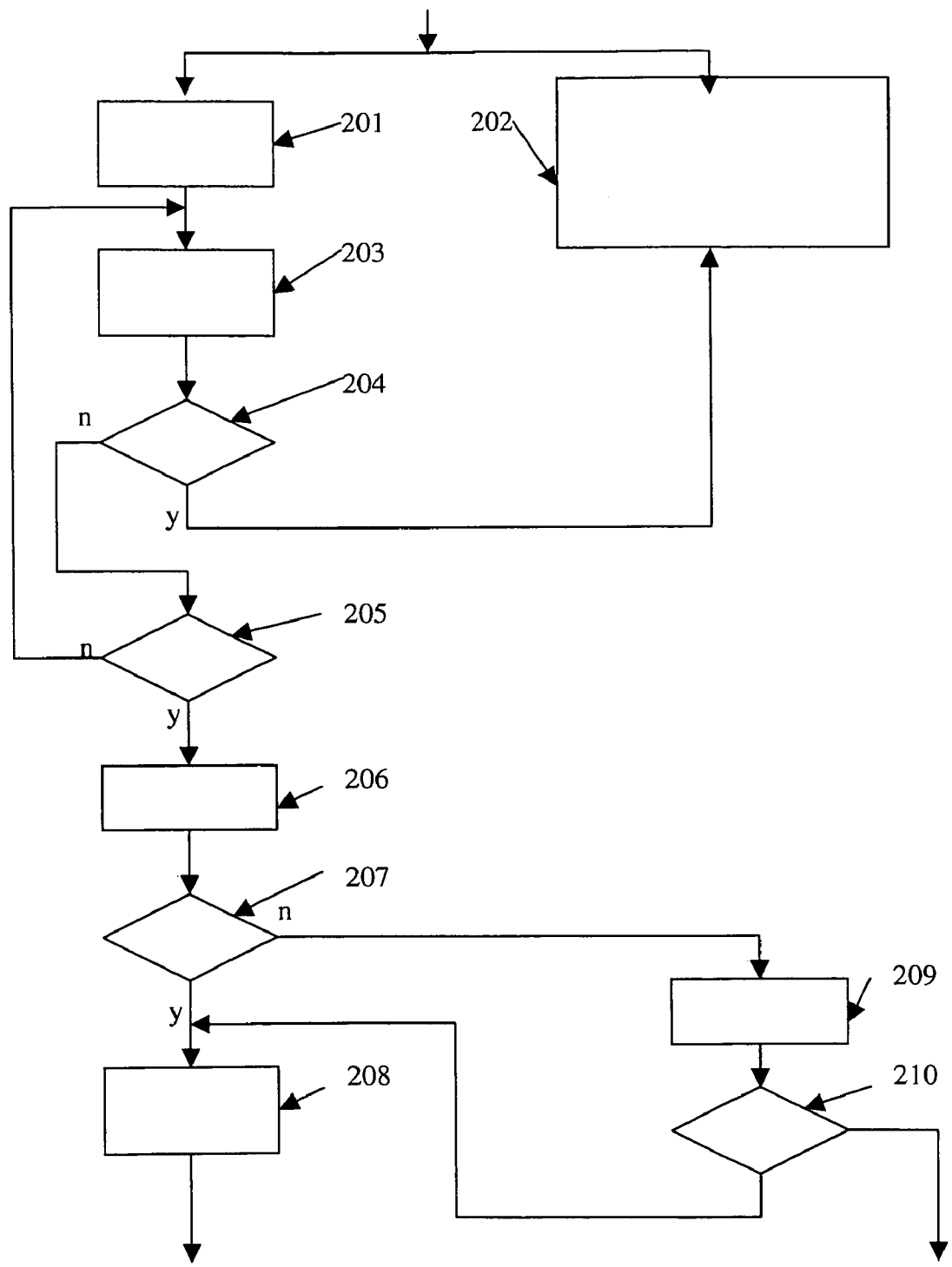
FIG. 2 shows the flowchart to be used in Step 105 of FIG. 1.

FIG. 2 shows the flowchart to be used in Step 105 of FIG. 1, referred to there as "A".

In Step 201, a PTT reference value ($PTT_{ref}$) is determined during the initial phase of dialysis.

Step 202 provides for data storage following each oscillometric BP measurement during dialysis.
 Measurement 1: ($t_1$, $BP_1$, $PTT_1$)
 Measurement 2: ($t_2$, $BP_2$, $PTT_2$)
 Measurement n: ($t_n$, $BP_n$, $PTT_n$)

These pairs of measured values are recorded, in the first place, at cyclic intervals of, for example, 30 minutes (parallel to the checks conducted in Steps 201, 203 and 204). In the second place, a pair of measured values of this kind may need to be recorded as a result of the check performed in Step 204. The check performed in Step 204 then initiates a blood-pressure measurement at this point in time.

In Step 203, the relative PTT change according to Equation (9) is determined for each new PTT value PTT(i)

$$relPttChg = \frac{|PTT_{Ref} - PTT(i)|}{PTT_{Ref}} \cdot 100 \quad (9)$$

In Step 204, a check is performed as to whether the PTT change has resulted in a threshold being exceeded. In the embodiment described here, this check is effected by determining the relative change; however, a check may also be performed by determining the absolute change.

$$relPttChg \geq TH_{PttChg} \quad (10)$$

where $TH_{PttChg}$ is the pre-defined threshold for the relative PTT change.

The exceeding of a threshold signalizes the occurrence of a BP drop; as provided for in Step 202, an oscillometric BP measurement is activated and the result stored.

If the check performed in Step 204 does not show that the threshold has been exceeded, the next Step (205) is executed, which consists in checking whether the therapy session has been terminated.

If this is not the case, Step 203 is executed once more, in which the PTT change is again checked.

If a therapy termination is recognized, Step 206 is executed. Maximum and minimum BP values, along with the corresponding PTT values, are determined from the stored data:

$$BP_{min1} = \text{Min}(BP_1, BP_1, \ldots, BP_n) \Rightarrow$$
$$PTT_{min1} = PTT|_{BP=BP\,min1}$$

$$BP_{max1} = \text{Max}(BP_1, BP_1, \ldots, BP_n) \Rightarrow$$
$$PTT_{max1} = PTT|_{BP=BP\,max1}$$

In this embodiment, the parameters are determined using two pairs of measured values:

(Date$_{max1}$,BP$_{max1}$,PTT$_{max1}$) and (Date$_{min1}$,BP$_{min1}$, PTT$_{min1}$)

Following transfer of the variables
Date$_{min}$=Date$_{min\ 1}$, BP$_{min}$=BP$_{min\ 1}$, PTT$_{min}$=PTT$_{min\ 1}$
Date$_{max}$=Date$_{max\ 1}$, BP$_{max}$=BP$_{max\ 1}$, PTT$_{max}$=PTT$_{max\ 1}$
a check is performed in Step 207 as to whether the criteria $$BP_{max}-BP_{min} \geq TH_{Bp}$$

$$PTT_{min}-PTT_{max} \geq TH_{Ptt}$$

are fulfilled. TH$_{Ptt}$ is a pre-defined threshold value for the PTT difference as absolute pulse-wave-transit-time deviation, and TH$_{Bp}$ is a pre-defined threshold value for the blood-pressure difference as absolute blood-pressure deviation. It is also possible to use relative deviations instead of absolute deviations.

If it is established in Step 207 that these criteria are fulfilled, Step 208 is executed, in which the parameters m and n in Equation (I) are determined according to Equations (7) and (6).

If, in the check performed in Step 207, it is established that at least one of the two criteria is not fulfilled, it is concluded—according to this embodiment—that the data from the current therapy session are not sufficiently suitable for parameter determination. In this case, Step 209 is executed, in which a "data optimization" is performed.

$$BP_{min}=\mathrm{Min}(BP_{min\ 0},BP_{min\ 1}),PTT_{min},\mathrm{Date}_{min}$$

$$BP_{max}=\mathrm{Max}(BP_{max0},BP_{max1}),PTT_{max},\mathrm{Date}_{max}$$

This optimization procedure comprises comparing the data with data obtained in earlier measurements, which may have been stored, for example, on a patient card. So as to ensure the currency of the measured values, at least the value triplet of the current measurement is used.

Subsequently, in Step 210, the criteria are checked again as in Step 207, this time with the newly determined data. In addition, a third threshold value TH$_{Date}$ is inserted on account of the time variability of Equation (1):

$$|\mathrm{Date}_{max}-\mathrm{Date}_{min}| \leq TH_{Date}$$

If the check performed in Step 210 shows that, with the new data, the criteria are fulfilled, the constants m and n in Equation (1) are determined according to Equations (7) and (6).

If the check performed in Step 210 shows that, even with the new data, the criteria are not yet fulfilled, the program flow is terminated.

Figure 3:
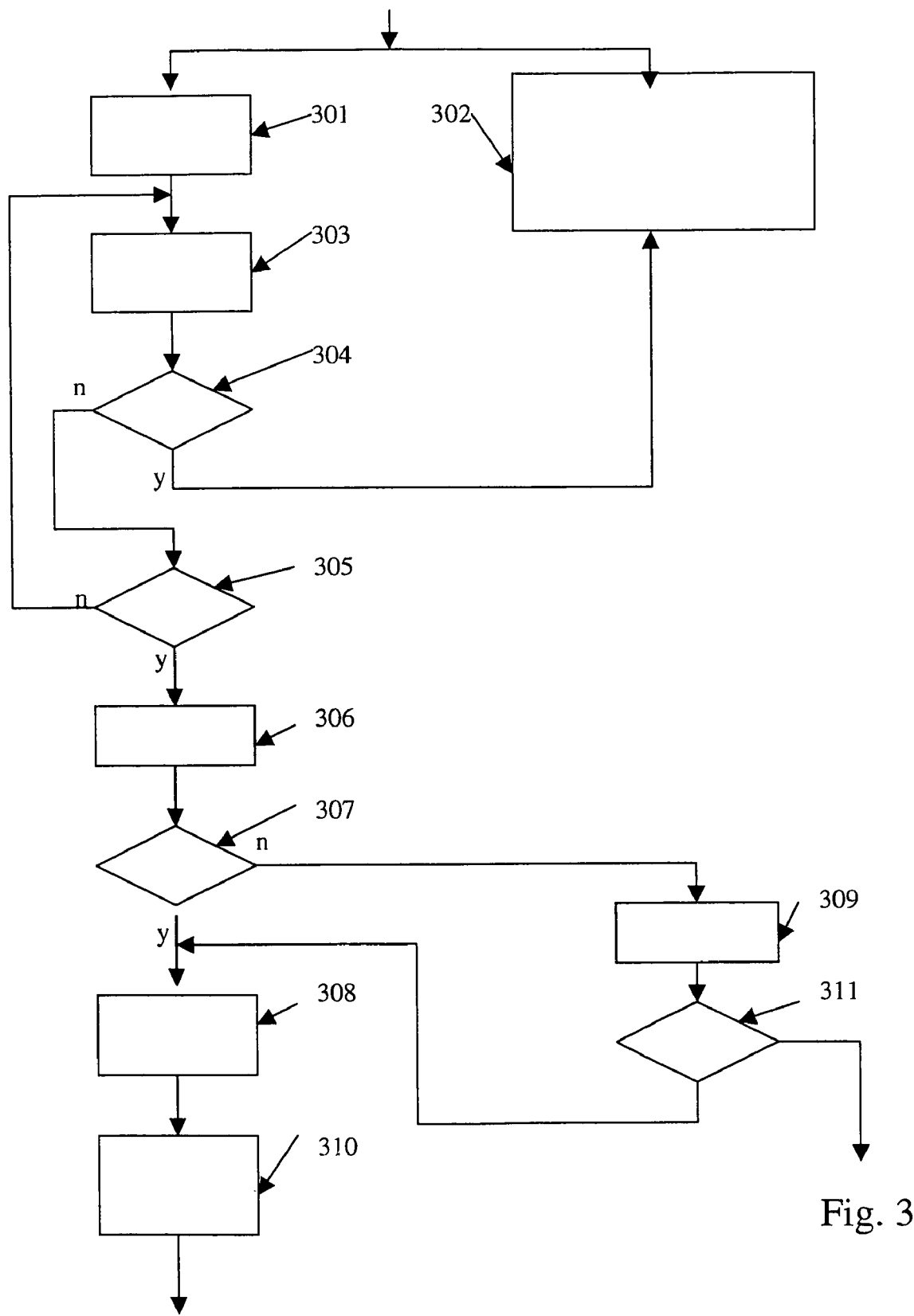
FIG. 3 shows the flowchart to be used in Step 104 of FIG. 1.

FIG. 3 shows the flowchart to be used in Step 104 of FIG. 1, referred to there as "B".

The Steps 301-308 in the flowchart shown in FIG. 3 correspond to the comparable Steps 201-208 in the flowchart of FIG. 2. The only difference in the embodiment described here is that values for the parameters m and n are already available, so that for checking the threshold value in Step 304, blood-pressure values can be determined directly from the PTT values using the already-determined parameters m and n. The threshold values can thus be related directly to the blood pressure.

It can be seen that Step 308 is followed by a further step, Step 310. In this step, the parameters m and n may be determined anew. The parameters m and n are estimated in this step by a weighted combination of the parameters m and n calculated during the current therapy session with the previously calculated parameters m0 and n0. The estimation is performed using the following Equations 14 and 15:

$$m=\alpha \cdot m+(1-\alpha) \cdot m_0 \quad 0 \leq \alpha \leq 1 \quad (14)$$

$$n=\beta \cdot n+(1-\beta) \cdot n_0 \quad 0 \leq \beta \leq 1 \quad (15)$$

where α and β are two pre-defined parameters which themselves are a function of other variables, e.g. of the time or also of the respective pressure differences.

If, in the check performed in Step 307, it is established that at least one of the criteria is not fulfilled, it is concluded—according to this embodiment—that the data from the current therapy session, on their own, are not sufficiently suitable for parameter determination.

In this case, Step 309 is executed, in which a "data optimization" is performed.

$$BP_{min}=\mathrm{Min}(BP_{min\ 0},BP_{min\ 1}),PTT_{min},\mathrm{Date}_{min}$$

$$BP_{max}=\mathrm{Max}(BP_{max0},BP_{max1}),PTT_{max},\mathrm{Date}_{max},$$

To this end, pairs of measured values obtained during earlier therapy sessions are required. Only such pairs of measured values as were recorded at a time within a given time window are eligible. These pairs of measured values are used to determine the minimum and maximum blood-pressure values. A check as in Step 307 is now performed again on the basis of these values to establish whether the criteria are fulfilled. If this is the case, Step 308 is executed.

The invention claimed is:

1. Dialyser having a blood-pressure measuring unit assigned to said dialyser, a pulse-wave-transit-time measuring system assigned to said dialyser and an evaluation unit, wherein the evaluation unit is configured such that the parameters (m, n) describing the relationship between the pulse wave transit time and the blood pressure are determined (208, 308) from measurements made by the blood-pressure measuring unit and simultaneous measurements made by the pulse-wave-transit-time measuring system, whereby at least two of these pairs of measured values are measured at times when the absolute and/or the relative deviation of the pulse wave transit time and/or of the blood pressure is above a threshold value.

2. Dialyser according to claim 1, wherein the maximum and minimum blood pressures measured, together with the corresponding measured pulse wave transit times, can be used to determine the parameters describing the relationship between the pulse wave transit time and the blood pressure (208, 308).

3. Dialyser according to claim 1, wherein only such pairs of measured values as are obtained within a given time window can be used to determine the parameters describing the relationship (309).

4. Dialyser according to claim 1, wherein a data input unit is assigned or assignable to the dialyser, said input unit serving to supply pairs of values obtained by the measuring unit and the measuring system during earlier therapy sessions with the same patient to the evaluation unit from a storage medium.

5. Dialyser according to claim 4, wherein the data input unit is simultaneously a data output unit with which the pairs of measured values from the current therapy session are written onto the storage medium.

6. Dialyser having a blood-pressure measuring unit assigned to said dialyser, a pulse-wave-transit-time measuring system assigned to said dialyser and an evaluation unit, wherein the evaluation unit is configured such that the parameters (m, n) describing the relationship between the pulse wave transit time and the blood pressure are determined (208, 308) from measurements made by the blood-pressure measuring unit and simultaneous measurements made by the pulse-wave-transit-time measuring system, whereby at least two of these pairs of measured values are measured at times when the absolute and/or the relative deviation of the pulse wave transit time and/or of the blood pressure is above a threshold value; and wherein for parameter determination, the pairs of measured values can be weighted (310) according to the times at which the values were recorded, the weighting being weaker for pairs of measured values recorded further back in time.

7. Method of determining the parameters describing the relationship between a pulse-wave-transit-time signal and a blood-pressure-measurement signal, wherein the parameters (m, n) describing the relationship between the pulse wave transit time and the blood pressure are determined (208, 308) from a plurality of blood-pressure-measurement-signal values and simultaneous pulse-wave-transit-time values, at least two of these pairs of measured values being obtained at points in time when the absolute and/or the relative deviation of the pulse-wave-transit-time and/or of the blood-pressure-measurement-signal is above a threshold value.

8. Method according to claim 7, wherein the maximum and minimum blood pressures measured, together with the corresponding measured pulse wave transit times, are used to determine the parameters describing the relationship between the pulse wave transit time and the blood pressure (208, 308).

9. Method according to claim 7, wherein only such pairs of measured values as are obtained within a given time window are used to determine the parameters describing the relationship (309).

10. Method of determining the parameters describing the relationship between a pulse-wave-transit-time signal and a blood-pressure-measurement signal, wherein the parameters (m, n) describing the relationship between the pulse wave transit time and the blood pressure are determined (208, 308) from a plurality of blood-pressure-measurement-signal values and simultaneous pulse-wave-transit-time values, at least two of these pairs of measured values being obtained at points in time when the absolute and/or the relative deviation of the pulse-wave-transit-time and/or of the blood-pressure-measurement-signal is above a threshold value; and wherein for parameter determination, the pairs of measured values are weighted (310) according to the times at which the values were recorded, the weighting being weaker for pairs of measured values recorded further back in time.

\* \* \* \* \*